United States Patent [19]

Ghelardoni et al.

[11] 4,296,124
[45] Oct. 20, 1981

[54] PHARMACEUTICAL METHODS

[75] Inventors: Mario Ghelardoni; Vittorio Pestellini; Piero Del Soldato; Giovanna Volterra; Alberto Meli, all of Florence, Italy

[73] Assignee: A. Menarini S.A.S., Italy

[21] Appl. No.: 176,867

[22] Filed: Aug. 11, 1980

[30] Foreign Application Priority Data

Aug. 10, 1979 [IT] Italy ................................ 9513 A/79

[51] Int. Cl.³ .......................................... A61K 31/34
[52] U.S. Cl. ................................................ 424/285
[58] Field of Search .................. 260/346.22; 424/285

[56] References Cited

FOREIGN PATENT DOCUMENTS 1160925 8/1969 United Kingdom .

OTHER PUBLICATIONS

Ghelardoni et al., Bull. Chem. Farm., 109 (1970), pp. 48-59.
Pisanti et al., Il Farmaco-Ed. Sc., vol. 26 (4) (1970), pp. 312-321.

Primary Examiner—Henry R. Jiles
Assistant Examiner—Bernard Dentz
Attorney, Agent, or Firm—McGlew and Tuttle

[57] ABSTRACT

A compound for use as a normolipidemizer and/or a platelet anti-binder in therapy, and pharmaceutical compositions containing the compound. The compound comprises (2-benzofuryl)-(p-chlorophenyl)-carbinol (Chloridarol, DCI) of formula:

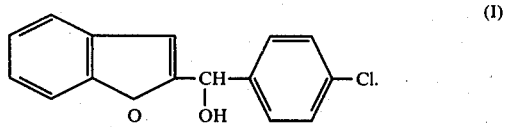

(I)

4 Claims, No Drawings

PHARMACEUTICAL METHODS

BACKGROUND OF THE INVENTION

1. Field of the Invention

The present invention relates to the use in therapy of the compound (2-benzofuryl)-(p-chlorophenyl)-carbinol (Chloridarol, DCI) of formula:

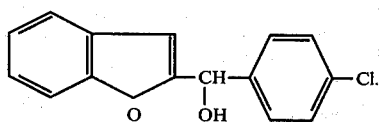
(I)

2. Description of the Prior Art

Chloridarol itself is known (see for example copending Italian Patent Application No. 93 File No. 86 of Feb. 22, 1963; British Patent Specification No. 1,160,925; Belgium Patent Specification No. 644,178 and Spanish Patent Specification No. 296,706 in the name of A. Menarini S.a.s., Florence). This compound is known to have therapeutic properties at the cardiac level and it is widely used in therapy in this field in various countries.

SUMMARY OF THE INVENTION

According to the present invention there is provided a compound for use as a normolipidemizer, the compound comprising (2-benzofuryl)-(p-chlorophenyl)-carbinol of formula:

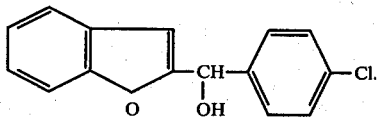
(I)

Further according to the invention, there is provided a compound for use as a platelet anti-binder, the compound comprising (2-benzofuryl)-(p-chlorophenyl)-carbinol of formula I:

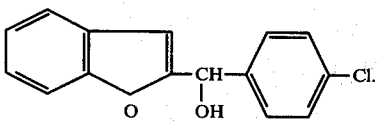
(I)

Further, according to the invention, there is provided a pharmaceutical composition having an activity selected from the group conisting of normolipidemic and platelet anti-binding activities, the composition comprising the compound (2-benzofuryl)-(p-chlorophenyl)-carbinol of formula:

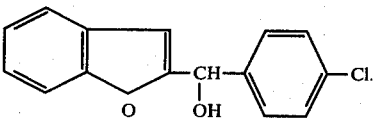
(I)

as active ingredient and a pharmaceutical vehicle or excipient.

DETAILED DESCRIPTION OF THE PREFERRED EMBODIMENTS

In pharmacological and clinical tests, chloridarol displays a marked normolipidemizing and platelet anti-binding activity.

Pharmacological Testing

The normolipidemizing activity has been investigated pharmacologically, by means of the fructose hyperglyceridemia test in rats according to E. A. Nikkila and K. Ojola, Life Sci., 4, 937 (1965).

The platelet anti-binding activity was investigated by means of a test which measures the variation of the number of platelets in circulation after administration of ADP (adenosine diphosphoric acid) to rats according to G. De Gaetano and A. E. Cavenaghi, Thrombosio Res. 10, 525 (1977).

In both tests Chloridarol displays an activity comparable to that of chlofibrate. However, the toxicity of chloridarol is at most half that of chlofibrate.

Clinical Testing

Treatment with Chloridarol at doses ranging from 250 to 2500 mg/day was given to 200 patients who exhibited dislipidemic syndromes characterised by a high plasmatic rate of triglycerides and cholesterol which was not reducible by dietetic treatment. The results obtained indicate that the compound is able to reduce the triglyceride and cholesterol blood rate to a statistically and clinically significant extent. Patients treated with Chloridarol at the doses stated above show, after a period of treatment ranging from 15 days to 3 months, a reduction of cholesterolemia of between 12 and 30% of the basal values and a reduction of triglyceridemia of between 15 and 50% of the basal values.

Chloridarol can be combined with an appropriate pharmaceutical carrier or excipient to form a pharmaceutical composition suitable for example, for oral, parenteral or rectal administration. The pharmaceutical composition may be supplied in units suitable for administration in a single dose or in repeated doses over a long period of time since it does not impair the function of the main organs and tracts.

We claim:

1. A method of causing normolipidemia in mammals by administering a normolipidemic amount of the compound (2-benzofuryl)-(p-chlorophenyl)-carbinol of formula I:

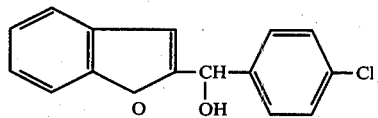
(I)

2. A method of decreasing platelet binding in mammals by administering an effective amount of the compound (2-benzofuryl)-(p-chlorophenyl)-carbinol of formula I:

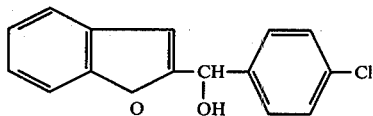
(I)

3. A method according to claims 1 or 2, wherein the amount is administered one of orally, parenterally and rectally.

4. A method according to claims 1 or 2, wherein a dosage of from 250 to 2,500 mg/day is administered to humans.

* * * * *